United States Patent [19]
Ji et al.

[11] Patent Number: 5,882,315
[45] Date of Patent: Mar. 16, 1999

[54] ULTRASONIC IMAGING METHOD AND IMAGE FOR DOPPLER TISSUE PARAMETERS

[75] Inventors: Ting-Lan Ji, San Jose; Ismayil Guracar, Redwood City, both of Calif.

[73] Assignee: Acuson Corporation, Mountain View, Calif.

[21] Appl. No.: 996,569

[22] Filed: Dec. 23, 1997

[51] Int. Cl.[6] ..................................................... A61B 8/00
[52] U.S. Cl. ........................................................... 600/553
[58] Field of Search ............................ 600/441, 453–458; 128/916

[56] References Cited

U.S. PATENT DOCUMENTS

| | | | |
|---|---|---|---|
| 5,285,788 | 10/1992 | Arenson . | |
| 5,513,640 | 5/1996 | Yamazaki et al. | 600/455 |
| 5,526,816 | 6/1996 | Arditi | 600/458 |
| 5,664,571 | 9/1997 | Yamazaki | 600/455 |
| 5,669,385 | 9/1997 | Pesque et al. | 128/916 |
| 5,720,291 | 2/1998 | Schwartz | 128/916 |
| 5,732,705 | 2/1998 | Yokoyama et al. | 600/458 |
| 5,735,281 | 4/1998 | Rafter et al. | 600/458 |

*Primary Examiner*—Francis J. Jaworski
*Attorney, Agent, or Firm*—Brinks Hofer Gilson & Lione

[57] ABSTRACT

An improved Doppler tissue imaging mode combines two Doppler image parameters developed as respective functions of receive signals acquired from a single firing event to generate a combined image parameter for display. In one example, the combined image parameter has a color hue that varies in a piecewise linear way with Doppler tissue velocity or Doppler tissue acceleration and a color value or intensity that varies linearly with Doppler tissue energy. Because the same firing events are used to develop both Doppler image parameters for a given region of tissue, high temporal and/or spatial resolution is made possible.

16 Claims, 4 Drawing Sheets

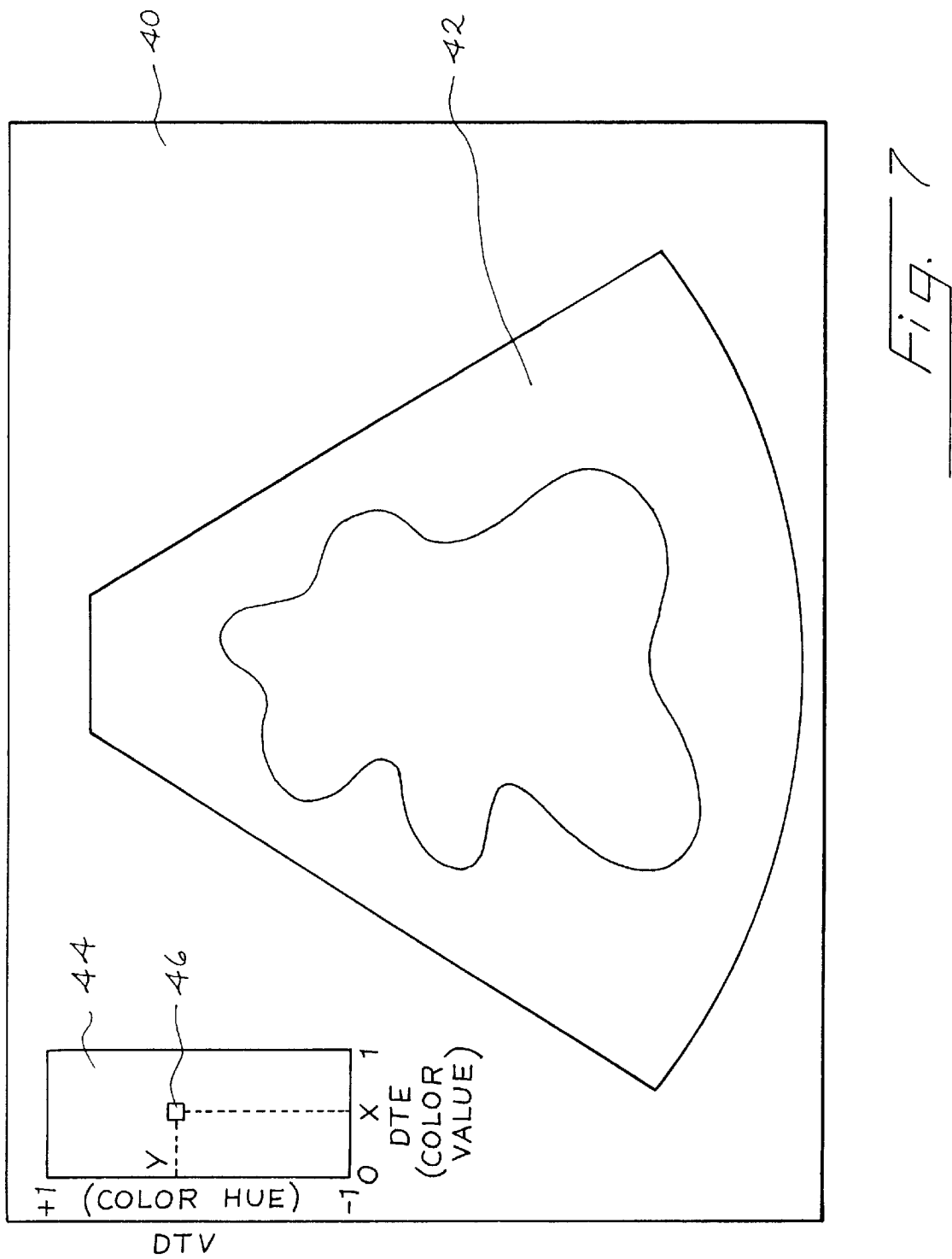

ULTRASONIC IMAGING METHOD AND IMAGE FOR DOPPLER TISSUE PARAMETERS

Background

This invention relates to improved methods and images for displaying Doppler tissue information in an ultrasonic imaging system.

Arenson et al. U.S. Pat. No. 5,285,788 discloses a Doppler tissue imaging method that forms an ultrasonic image of moving tissue. Stationary tissue is suppressed in the image since the Doppler signal is sensitive only to moving targets. In Doppler tissue imaging (DTI) standard clutter filters that block ultrasonic signals associated with low speed targets are made less restrictive, and the DTI image includes image information for slowly moving tissues such as the heart wall. Doppler tissue imaging can be performed using tissue velocity, energy or acceleration to form a two-dimensional image that is spatially coordinated with and superimposed on a conventional B-mode image. The B-mode image displays a tomographic image of both moving and stationary tissue, and the combination of DTI and B-mode images allows the selected Doppler tissue information to be displayed simultaneously with and superimposed on the tomographic B-mode image.

Doppler tissue imaging has an important role in a number of cardiology imaging areas such as endocardial border detection, myocardial wall motion investigations, regional wall motion investigations, and myocardial perfusion investigations. In many applications, high quality Doppler tissue imaging depends greatly on the temporal and spatial resolution of the combined image.

In conventional DTI, two separate frames of image information are acquired: a color Doppler frame and a spatially coordinated B-mode frame. These two frames of image information are then combined to produce the DTI/B-mode composite image described above. For each pair of frames (DTI and B-mode), time is spent in alternately firing B-mode acoustic lines and color Doppler mode acoustic lines. If the time required for acquiring one B-mode frame is $T_B$ and the time required for acquiring one Doppler frame is $T_{D1}$, the total DTI/B-mode composite frame requires $(T_B+T_D)$ for acquisition, and the corresponding frame rate is $1/(T_B+T_D)$. The temporal resolution of the composite frame is fundamentally limited in this way.

A need presently exists for methods for increasing the time and/or spatial resolution of DTI images.

SUMMARY

The present invention is defined by the following claims, and nothing in this section should be taken as a limitation on those claims.

By way of introduction, the preferred embodiment described below includes a method and system for forming an ultrasonic image of an imaged region. First and second Doppler image parameters of an imaged region are developed as respective functions of receive signals acquired from a single firing event. The first Doppler image parameter may be Doppler tissue velocity, Doppler tissue acceleration, or Doppler tissue energy. The second Doppler image parameter is typically indicative of Doppler tissue energy, either filtered or unfiltered, and it carries tomographic information regarding tissue structure. In the case where the first and second Doppler image parameters are both indicative of Doppler tissue energy, one is filtered and the other is unfiltered. Both of the first and second Doppler image parameters are acquired in the same imaging mode, i.e. both are from the harmonic imaging mode or both are from the fundamental imaging mode. The first and second Doppler image parameters are combined to form a combined image parameter. Preferably, the combined image parameter is displayed with a color hue that varies as a function of the first Doppler image parameter and a color value that varies as a function of the second Doppler image parameter. The ultrasonic image can include an image legend that displays a color hue/color value map associated with the ultrasound image.

Because both the first and second Doppler image parameters for a given region are acquired from a single firing event, the need to alternate between Doppler image acoustic lines and B-mode acoustic lines is eliminated. The spatial and/or temporal resolution of the combined image are thereby increased.

BRIEF DESCRIPTION OF THE DRAWINGS

FIG. 7 is a schematic view of an ultrasonic image generated with the system of FIG. 1.

DETAILED OF THE PRESENTLY PREFERRED EMBODIMENTS

Figure 1:
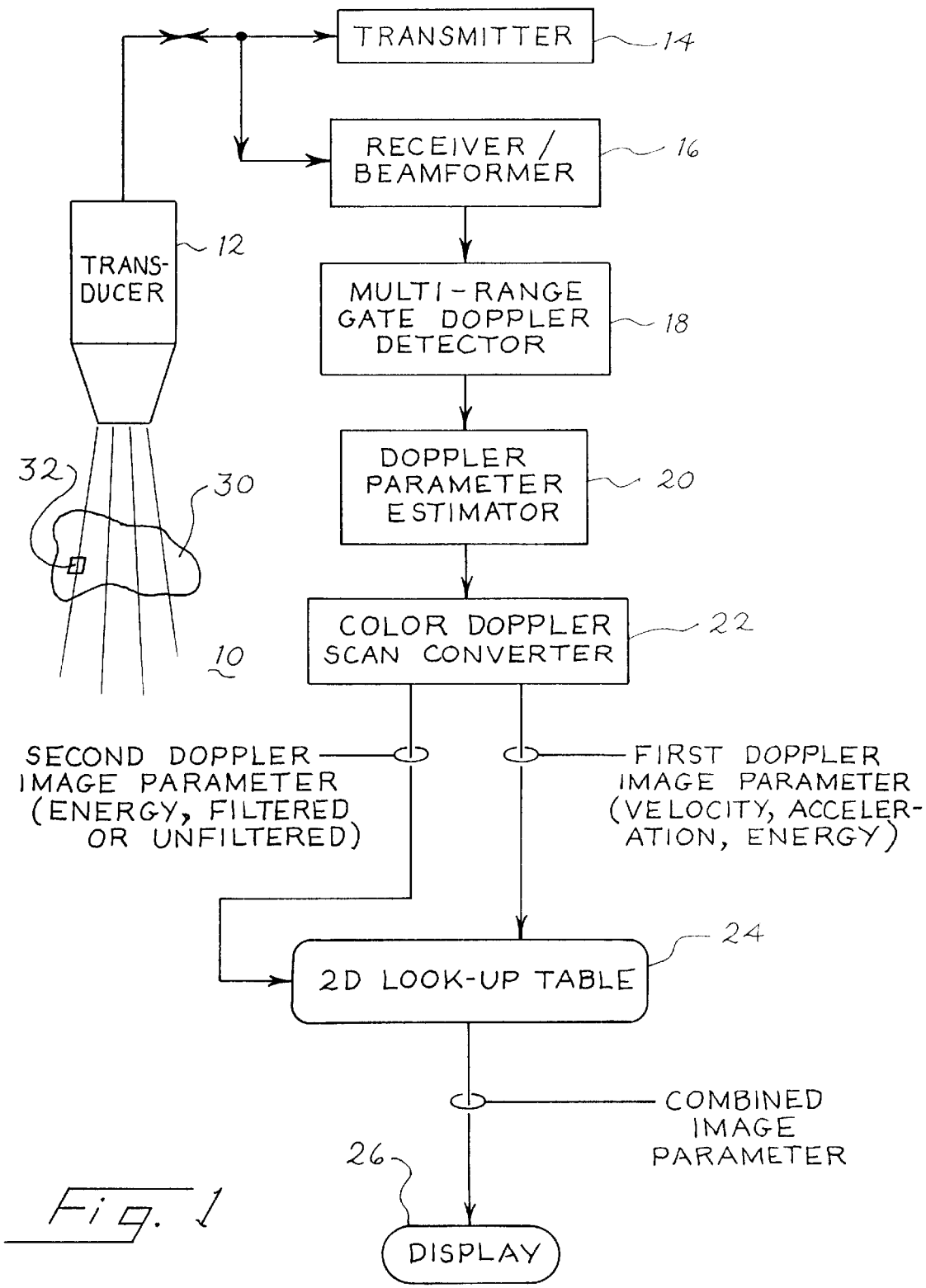
FIG. 1 is a block diagram of an ultrasonic imaging system suitable for use with this invention.

Turning now to the drawings, FIG. 1 shows an ultrasonic imaging system 10 that can be used to practice preferred embodiments of this invention. The ultrasonic imaging system 10 includes an ultrasonic transducer 12 that operates as a phased array in response to transmit signals generated by a transmitter 14. These transmit signals are preferably timed and phased in the conventional manner to cause ultrasonic energy emitted by the transducer 12 to be focused along acoustic scan lines which can be steered at least in the azimuthal direction., and optionally in the elevational direction as well.

Ultrasonic echo information is converted by the transducer 12 into electrical receive signals that are applied to a receiver/beamformer 16. The receiver/beamformer 16 applies appropriate delays and phase adjustments in a conventional manner to create beamformed signals along selected receive scan lines. In some embodiments, the receive scan lines may be aligned with respective ones of the transmit scan lines. Alternately, the receive scan lines may be offset with respect to the transmit scan lines. This invention can be used with the widest variety of transmitters, transducers and receiver/ beamformers, including single beam and multiple beam transmitters and receiver/ beamformers.

The receiver/beamformer 16 generates a beamformed output signal that is applied to a multi-range gate Doppler detector 18. The detected output of the detector 18 is applied to a Doppler parameter estimator 20 and a color Doppler scan converter 22. Preferably, the multi-range gate Doppler detector 18, the Doppler parameter estimator 20 and the color Doppler scan converter 22 are of the type described in Arenson et al. U.S. Pat. No. 5,285,788. As explained in the Arenson patent, conventional clutter filters are made less restrictive such that the Doppler image parameters generated by the color Doppler scan converter 22 are suitable for Doppler tissue imaging. Since the clutter filters have been designed to block only a narrow range of velocities around zero, the Doppler imaging parameters include Doppler signals for low speed tissue such as the heart wall.

The widest variety of devices can be used to implement the elements 12–22 described above. The transmitter 14 and the receiver/beamformer 16 can be formed as digital or analog signal processors. The Doppler parameter estimator 20 can use conventional auto correlation techniques as well known to those skilled in the art. Alternatively, the Doppler parameter estimator can estimate Doppler parameters using time shift information instead of Doppler information, as described in U.S. Pat. No. 4,928,698. In this approach, cross correlation techniques are substituted for conventional auto correlation techniques.

The color Doppler scan converter 22 supplies up to four Doppler imaging parameters as output signals: Doppler tissue velocity, Doppler tissue acceleration, Doppler tissue energy (filtered), and Doppler tissue energy (unfiltered). These Doppler image parameters are individually well-known to those skilled in the art and they can take many forms. For example, Doppler tissue velocity (DTV) can be derived from Doppler frequency shift, and the mean Doppler frequency or the estimate of Doppler wavelength can be used as an indication of Doppler tissue velocity. Therefore, it will be understood that whenever Doppler velocity or Doppler tissue velocity is referred to in this specification or the following claims, Doppler or Doppler tissue frequency or wavelength may be used instead. For simplicity, the term "Doppler tissue velocity" will be used broadly to include velocity, frequency and/or wavelength measures indicative of velocity. The term "Doppler tissue velocity" is intended broadly to encompass both instantaneous measures of velocity as well as average or mean measures of velocity. Doppler tissue acceleration (DTA) can be derived from Doppler tissue velocity by taking the velocity difference between two consecutive frames.

Doppler tissue energy (DTE) is a term intended broadly to encompass various measures of the amplitude, intensity or power of the Doppler information or time shift signals. In this context, power is the energy of such signals per unit time, and amplitude is proportional to the square root of power. For simplicity, the term "Doppler tissue energy" in this specification and the following claims is intended broadly to encompass energy and/or power and/or amplitude of the signal, and the last three terms are used interchangeably.

The Doppler tissue energy signal may be filtered or unfiltered. As used herein, a filtered DTE signal is a Doppler tissue energy signal that has been filtered with a high pass filter such as a conventional clutter filter, where the cutoff frequency of the filter is low enough that the filtered DTE signal includes signals associated with moving tissues (e.g. heart wall tissue). As used herein, an unfiltered DTE signal is a Doppler tissue energy that has not been filtered with such a high pass filter.

Returning to FIG. 1, the ultrasonic imaging system 10 includes a two dimensional lookup table 24 that is used to combine the first and second Doppler image parameters from the scan converter 22 to form a combined image parameter. This combined image parameter is supplied to a display 26. In this embodiment, the first Doppler image parameter is selected from the group consisting of Doppler tissue velocity, Doppler tissue acceleration, and Doppler tissue energy, (filtered or unfiltered). The second Doppler image parameter is a measure of Doppler tissue energy (filtered or unfiltered). When both of the Doppler image parameters correspond to Doppler tissue energy, one corresponds to DTE (filtered) and the other to DTE (unfiltered).

Figure 2:
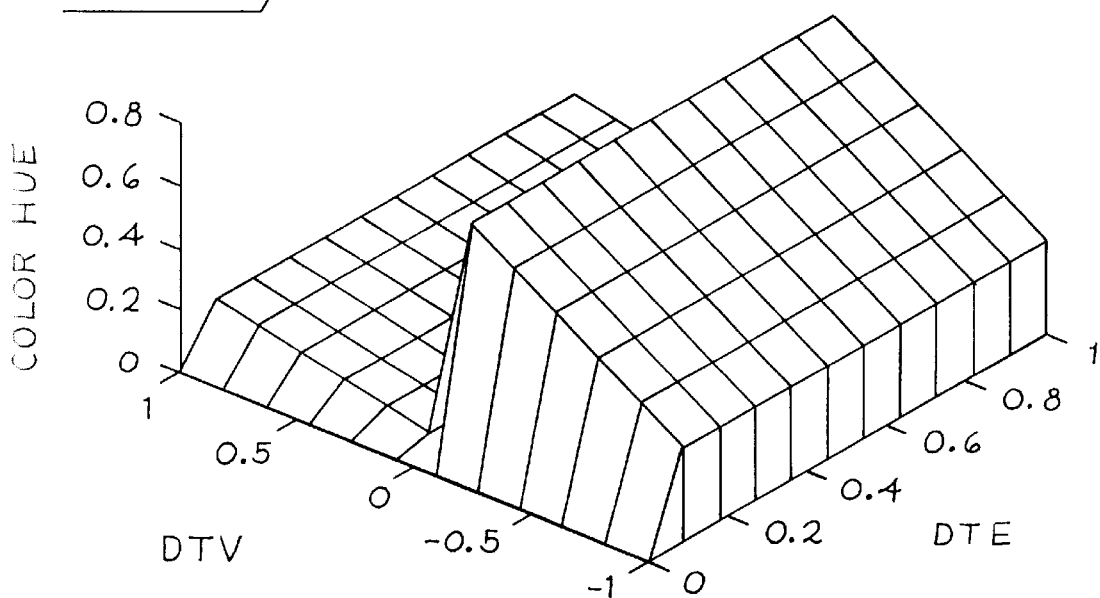
FIGS. 2 and 3 are schematic representations of color value and color hue maps suitable for use in designing the lookup table of FIG. 1.
Figure 3:
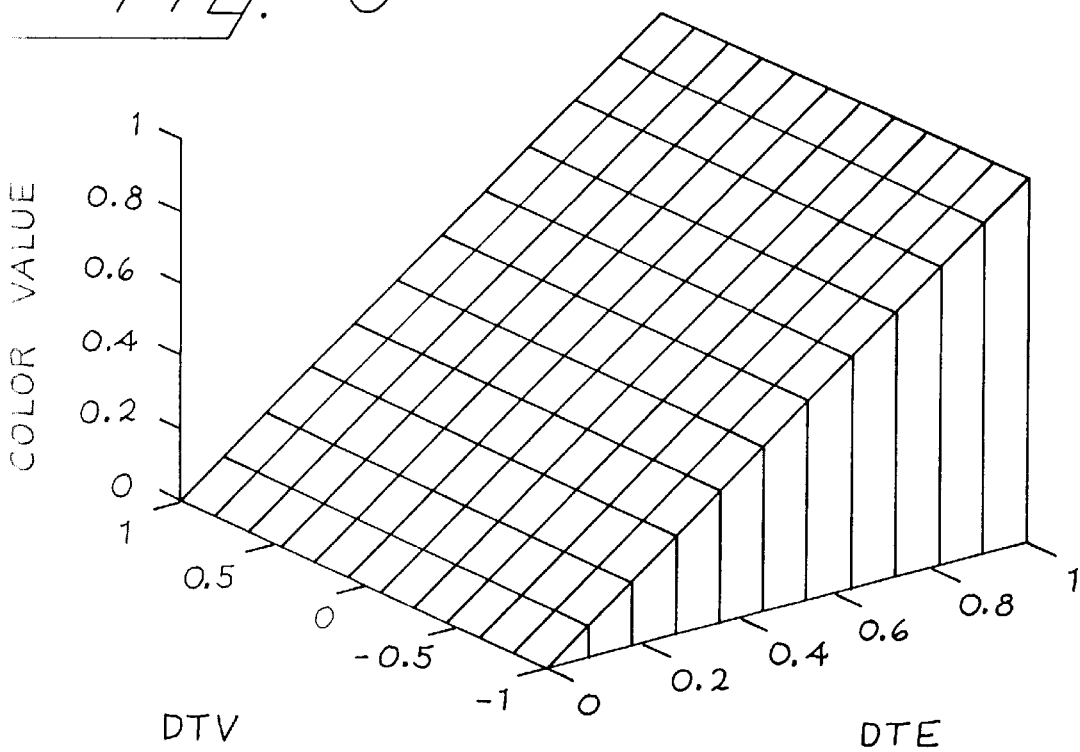
Figure 4:
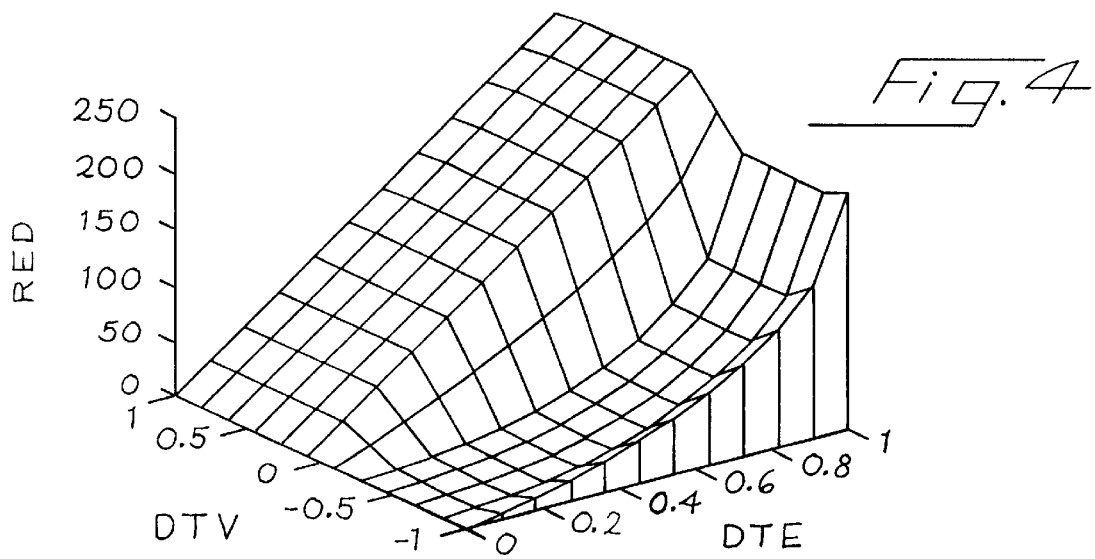
FIGS. 4–6 are schematic representations of red, green and blue color intensity maps suitable for use in the lookup table of FIG. 1.
Figure 5:
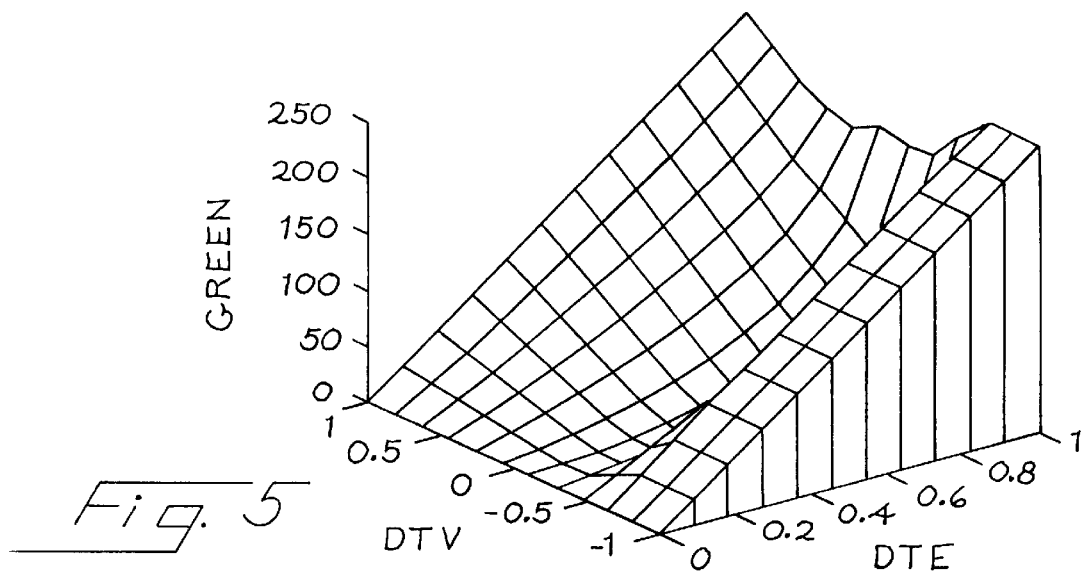
Figure 6:
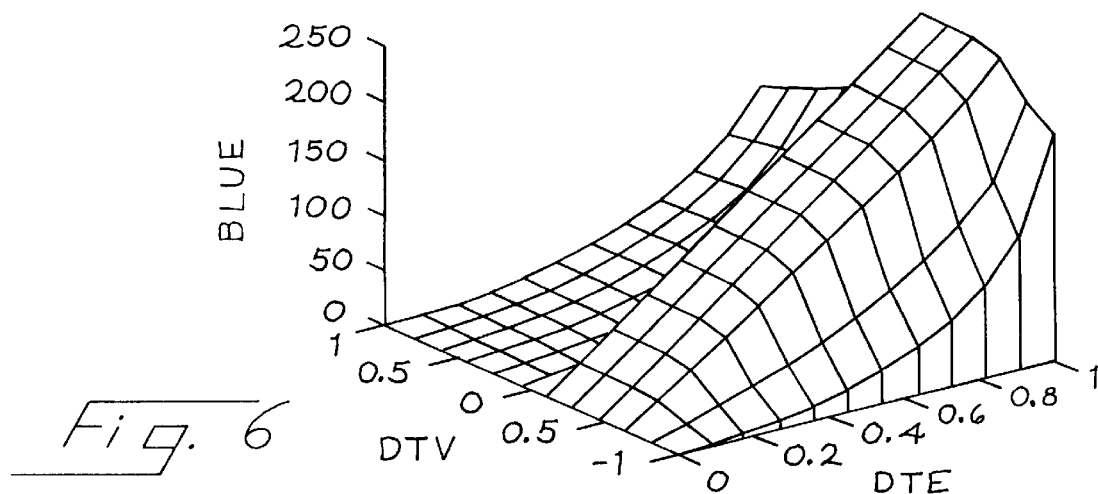

The look up table 24 of this embodiment is implemented as a 2-D color map that causes the color hue and the color value or color intensity of the combined image parameter to vary as a function of both the first and second Doppler image parameters. FIGS. 2–6 provide various representations of a suitable color map for the look up table 24. FIGS. 2 and 3 show the color map in HSV color space, while FIGS. 4–6 show the color map in RGB color space. In the example of FIGS. 2 through 6, the first Doppler image parameter is DTV and the second Doppler image parameter is DTE. As shown in FIG. 2, the color hue of the combined image parameter, (represented in the vertical axis) is a piecewise linear function of Doppler tissue velocity DTV, with the two linear pieces corresponding to the two directions of tissue velocity, but is substantially independent of the value of DTE. As shown in FIG. 3, the color value or intensity of the combined image parameter varies as a linear function of DTE and is insensitive to the value of DTV. In this embodiment, color saturation S is a constant and therefore not shown. Alternately, color saturation can be made variable, for example, as a function of color value.

In practice, the color map of FIGS. 2 and 3 is converted to RGB color space to form three correlated look up tables for the three primary colors, red, green and blue. Color maps shown in FIGS. 4, 5 and 6 define one exemplary embodiment of a suitable look up table for combining the first and second Doppler image parameters to form the combined image parameter. By way of example, the red, green and blue pixel values shown in FIGS. 4, 5 and 6 can be used as follows: DTV and DTE values for a given point in the region are used as addressing inputs to the look up tables shown schematically in FIGS. 4, 5 and 6 to select red, green and blue pixel values for the corresponding pixel of the displayed ultrasonic image. In the example of FIGS. 2–6, only subsample data are shown. The look up table 24 can be implemented using two dimensional linear interpolation between subsample data points as shown.

The mapping function from Doppler tissue velocity to color hue, and the mapping function from Doppler tissue energy to color value do not have to be linear as shown in FIGS. 2 and 3. Non-linear functions may also be used, though it is preferable that the mappings be reversible, i.e. each value of the combined image parameter is unambiguously associated with a single set of values for the first and second image parameters. The reversibility of the map guarantees that for each color pixel, one can decode its RGB values uniquely to its Doppler energy and velocity.

In this embodiment, the first and second Doppler image parameters are developed as respective functions of receive signals acquired from a single firing event for a given region of the imaged tissue. For example, considering the imaged tissue 30 of FIG. 1, echo signals from a given region 32 are coherently summed in the receiver/beamformer 16 and are then applied to the detector 18, the estimator 20 and the scan converter 22, such that the first Doppler image parameter and the second Doppler image parameter associated with the region 32 are developed as respective functions of echoes associated with a single firing event In effect, the Doppler tissue energy signal substitutes for a conventional B-mode signal. In this way, the need for a B-mode image signal is eliminated in this mode of operation, and the time to create an image frame of the combined image parameter is simply the time $T_D$ required to acquire a single Doppler frame.

As used herein, an image parameter is said to be developed as a function of receive signals from a first firing event both (1) when only receive signals from the first firing event are used to develop the image parameter, and (2) when receive signals from the first firing event are used with receive signals from other firing events to develop the image parameter. For example, the image parameters DTV and DTE are developed as respective functions of receive signals $R_n$ acquired from firing event N even though DTE may be developed as a function of only the receive signals $R_n$, while DTV may be developed as a function of the receive signals $R_n$ as well as one or more sets of receive signals $R_m$, $R_o$ associated with other firing events.

Both of the first and second Doppler image parameters are acquired using a common imaging mode, either a harmonic imaging mode or a fundamental imaging mode. In the harmonic imaging mode the echo signals used to form the first and second Doppler image parameters correspond to echoes at a harmonic of the fundamental ultrasonic frequency supplied to the transducer 12 by the transmitter 14. In the fundamental imaging mode the first and second Doppler image parameters are formed from echo information linearly scattered by the image tissue, without frequency shift at the scattering interface. As used herein, harmonic is intended broadly to include sub-harmonics, fractional harmonics, and integral harmonics greater than 1.

FIG. 7 shows an example of a display 40 generated by the system 10. The display 40 includes two images in this embodiment. The first is an ultrasonic image 42 of the imaged region. In the ultrasonic image 42 the combined image parameter described above is displayed, having a color hue that varies as a linear or proportional function of the first Doppler image parameter and a color intensity or value that varies linearly or proportionally with Doppler tissue energy, the second Doppler image parameter.

The second image 44 is a color legend that assists the user in interpreting the color hue and color value displayed at individual pixels of the ultrasonic image 42. In the legend 44 of this embodiment, one of the axes (the x-axis in this example) varies progressively with the second Doppler image parameter (minimum to maximum DTE in this example), while the other axis (the y-axis in this example) varies progressively with the first Doppler image parameter (minimum to maximum DTV in this example). For each pixel 46 in the legend 44, there is an associated x and y coordinate. The color intensity or color value of the pixel 46 is determined by the x coordinate, and the color hue for the pixel 46 is determined by the y coordinate using the color maps described above in conjunction with FIGS. 4 through 6.

In another mode of operation both the first and second Doppler image parameters of the display and the legend vary as a function of filtered and unfiltered Doppler tissue energy, respectively.

The tomographic information of tissue, conventionally displayed by B-mode image frame, is now provided in the ultrasonic image 42 by the second Doppler image parameter (unfiltered Doppler tissue energy in this example). Since B-mode imaging is eliminated, a substantial amount of time can be saved. This allows a substantial increase in the frame rate and an associated improvement in temporal resolution. Alternately, the saved time can be used to fire more Doppler lines per frame, and thereby to improve spatial resolution. Of course, the saved time can be distributed appropriately to improve both temporal and spatial resolution simultaneously.

As described above, the system 10 provides improved temporal and/or spatial resolution as compared to a conventional DTI system, which combines B-mode and Doppler frames. The system 10 eliminates the need for B-mode frames and provides the desired graphic information of the tissue by substituting a DTE image parameter for the B-mode image parameter. In some applications, the frame rate can be increased by a factor of two assuming a constant spatial resolution is maintained. This advantage is obtained because the second image parameter DTE carries tissue tomographic information, and both Doppler image parameters are obtained simultaneously from a single DTI frame.

Of course, many changes and modifications are possible to the preferred embodiment described above. The system 10 can operate using polar or Cartesian coordinates, and the first and second Doppler image parameters may be combined using hardware other than look up tables. For example, various beamforming and Doppler signal processing techniques can be used including both analog and digital techniques. When a two-dimensional look up table is used, it can be implemented physically as a one-dimensional table, using appropriate addressing logic. Also, the combined image parameter may be a function of other parameters in addition to the first and second Doppler image parameters discussed above. As used herein, a parameter that varies as a function of two or more parameters is therefore said to vary as a function of each of these parameters individually.

The foregoing detailed description has described only a few of the many forms that this invention can take. For this reason it is intended that this detailed description be regarded as an illustration and not as a limitation of the invention. It is only the following claims, including all equivalents, that are intended to define the scope of this invention.

We claim:

1. A method for forming an ultrasonic image of an imaged region, said method comprising the following steps:

(a) developing first and second Doppler image parameters of an imaged region, both said first and second Doppler image parameters varying as respective functions of receive signals acquired from a single firing event; said first Doppler image parameter selected from the group consisting of: Doppler tissue velocity, Doppler tissue acceleration and combinations thereof; said second Doppler image parameter indicative of Doppler tissue energy; said first and second Doppler image parameters both having a common imaging mode selected from the group consisting of: a harmonic imaging mode and a fundamental imaging mode;

(b) combining the first and second Doppler image parameters to form a combined image parameter.

2. A method for forming an ultrasonic image of an imaged region, said method comprising the following steps:

(a) developing first and second Doppler image parameters of an imaged region, both said first and second Doppler image parameters varying as respective functions of receive signals acquired from a single firing event; said first Doppler image parameter selected from the group consisting of: Doppler tissue velocity, Doppler tissue acceleration and combinations thereof; said second Doppler image parameter indicative of Doppler tissue energy; and (b) combining the first and second Doppler image parameters to form a combined image parameter, said combined image parameter characterized by a color hue that varies as a function of the first Doppler image parameter and by a color value that varies as a function of the second Doppler image parameter.

3. A method for forming an ultrasonic image of an imaged region, said method comprising the following steps:

(a) developing first and second Doppler image parameters of an imaged region, both said first and second Doppler image parameters varying as respective functions of receive signals acquired from a single firing event; said first and second Doppler image parameters both having a common imaging mode selected from the group consisting of: a harmonic imaging mode and a fundamental imaging mode; one of said Doppler image parameters indicative of filtered Doppler tissue energy; and the other of said Doppler image parameters indicative of unfiltered Doppler tissue energy; and (b) combining the first and second Doppler image parameters to form a combined image parameter.

4. A method for forming an ultrasonic image of an imaged region, said method comprising the following steps:

(a) developing first and second Doppler image parameters of an imaged region, both said first and second Doppler image parameters varying as respective functions of receive signals acquired from a single firing event; one of said Doppler image parameters indicative of filtered Doppler tissue energy; and the other of said Doppler image parameters indicative of unfiltered Doppler tissue energy;

(b) combining the first and second Doppler image parameters to form a combined image parameter said combined image parameter characterized by a color hue that varies as a function of the first Doppler image parameter and by a color value that varies as a function of the second Doppler image parameter.

5. The invention of claim 1 or 2 wherein said second Doppler image parameter is indicative of filtered Doppler tissue energy.

6. The invention of claim 1 or 2 wherein said second Doppler image parameter is indicative of unfiltered Doppler tissue energy.

7. The invention of claim 1 or 3 wherein the common imaging mode is the fundamental imaging mode.

8. The invention of claim 1 or 3 wherein the combined image parameter is characterized by a color hue that varies as a function of the first Doppler image parameter and by a color value that varies as a function of the second Doppler image parameter.

9. The invention of claim 8 wherein the color value varies as a linear function of the second Doppler image parameter.

10. The invention of claim 8 wherein the color hue varies as a piecewise linear function of the first Doppler image parameter.

11. The invention of claim 2 or 4 wherein the color value varies as a linear function of the second Doppler image parameter.

12. The invention of claim 2 or 4 wherein the color hue varies as a piecewise linear function of the first Doppler image parameter.

13. The invention of claim 1, 2, 3, or 4 wherein the first Doppler image parameter is indicative of Doppler tissue velocity.

14. The invention of claim 1, 2, 3, or 4 wherein the first Doppler image parameter is indicative of Doppler tissue acceleration.

15. The invention of claim 2 wherein the color hue of the combined image parameter is a piecewise linear function of Doppler tissue acceleration.

16. The invention of claim 1, 2, 3 or 4 wherein step (b) comprises the step of applying a reversible mapping function to the first and second Doppler image parameters to form the combined image parameter.

* * * * *

UNITED STATES PATENT AND TRADEMARK OFFICE
CERTIFICATE OF CORRECTION

PATENT NO. : 5,882,315
DATED : March 16, 1999
INVENTOR(S) : Ting-Lan Ji et al.

It is certified that error appears in the above-identified patent and that said Letters Patent is hereby corrected as shown below:

In column 1, line 43, change "$T_{D1}$" to --$T_D$--.

In column 2, line 32, after "DETAILED" insert --DESCRIPTION--.

In column 2, line 45, after "direction." delete "." (comma).

In column 4, line 64, after "event" insert "." (period).

In column 6, line 15, change "Cartesian" to --cartesian--.

In claim 4, line 12, after "parameter" insert --,-- (period).

Signed and Sealed this

Second Day of May, 2000

Attest:

Q. TODD DICKINSON

*Attesting Officer*         *Director of Patents and Trademarks*